United States Patent
Park

(10) Patent No.: US 7,238,170 B2
(45) Date of Patent: Jul. 3, 2007

(54) WARMER FOR MEDICAL TREATMENT AND ITS CONTROL METHOD

(76) Inventor: Koon Park, 508-603, Jukong Apt., 359-1 Joongkye1-Dong, Nowon-Gu, Seoul (KR) 139-860

( * ) Notice: Subject to any disclaimer, the term of this patent is extended or adjusted under 35 U.S.C. 154(b) by 761 days.

(21) Appl. No.: 10/240,552

(22) PCT Filed: Apr. 7, 2001

(86) PCT No.: PCT/KR01/00584

§ 371 (c)(1),
(2), (4) Date: Oct. 3, 2002

(87) PCT Pub. No.: WO01/78629

PCT Pub. Date: Oct. 25, 2001

(65) Prior Publication Data
US 2003/0176903 A1    Sep. 18, 2003

(30) Foreign Application Priority Data
Apr. 14, 2000   (KR) .............................. 2000-19737

(51) Int. Cl.
*A61F 7/12* (2006.01)
*A61B 18/14* (2006.01)

(52) U.S. Cl. ................. 604/113; 604/114; 607/106; 137/341

(58) Field of Classification Search ........ 604/113–114, 604/246–262, 6.13; 607/106, 113; 137/334, 137/340, 341, 375; 165/177, 178, 184; 392/465–496
See application file for complete search history.

(56) References Cited

FOREIGN PATENT DOCUMENTS

| JP | 08-206205 A | 8/1996 |
|---|---|---|
| JP | 09-248339 A | 9/1997 |
| KR | 98-87773 A | 12/1998 |

*Primary Examiner*—Catherine S. Williams
(74) *Attorney, Agent, or Firm*—John K. Park; Park Law Firm

(57) ABSTRACT

This invention prevents the danger of falling of body temperature by making the blood temperature similar to the body temperature in the injection of Ringer's solution fluid or blood transfusion, and also alleviates the patient's pain and improves the speed at which Ringer's solution fluid or blood enters the body. The warming device is much cheaper than previously released products, and small and light in weight, and allows blood or solution fluids to flow most effectively by allowing sufficient time for heat transfer as a pack type. The operation is convenient and sanitary in its single usage only. The inventive purpose has the methods of utilizing the temperature sensor in adjusting temperature by utilizing them PTC heating element's resistance specialty against the temperature as well as temperature sensor.

11 Claims, 8 Drawing Sheets

[Fig. 1a]
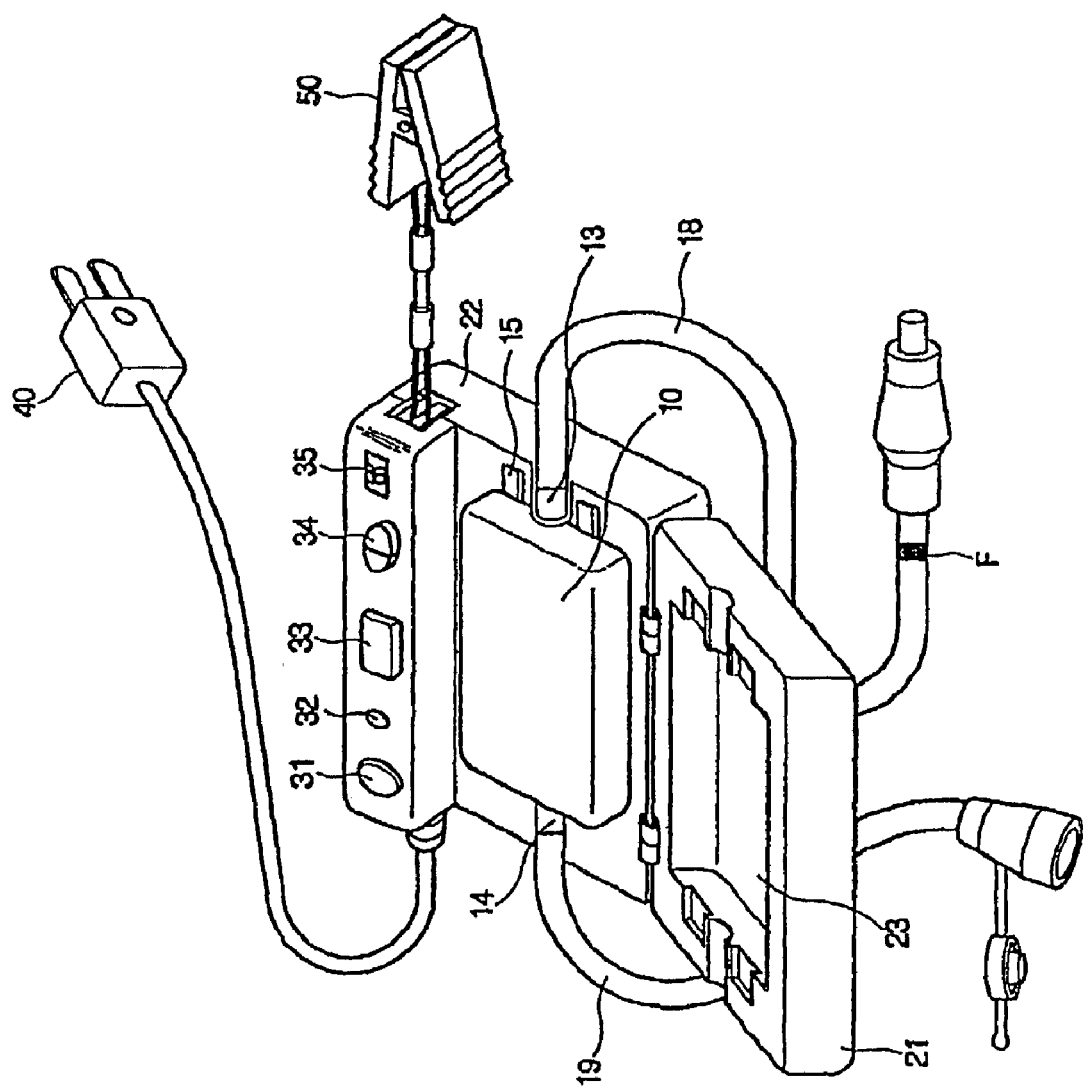

[Fig. 1b]
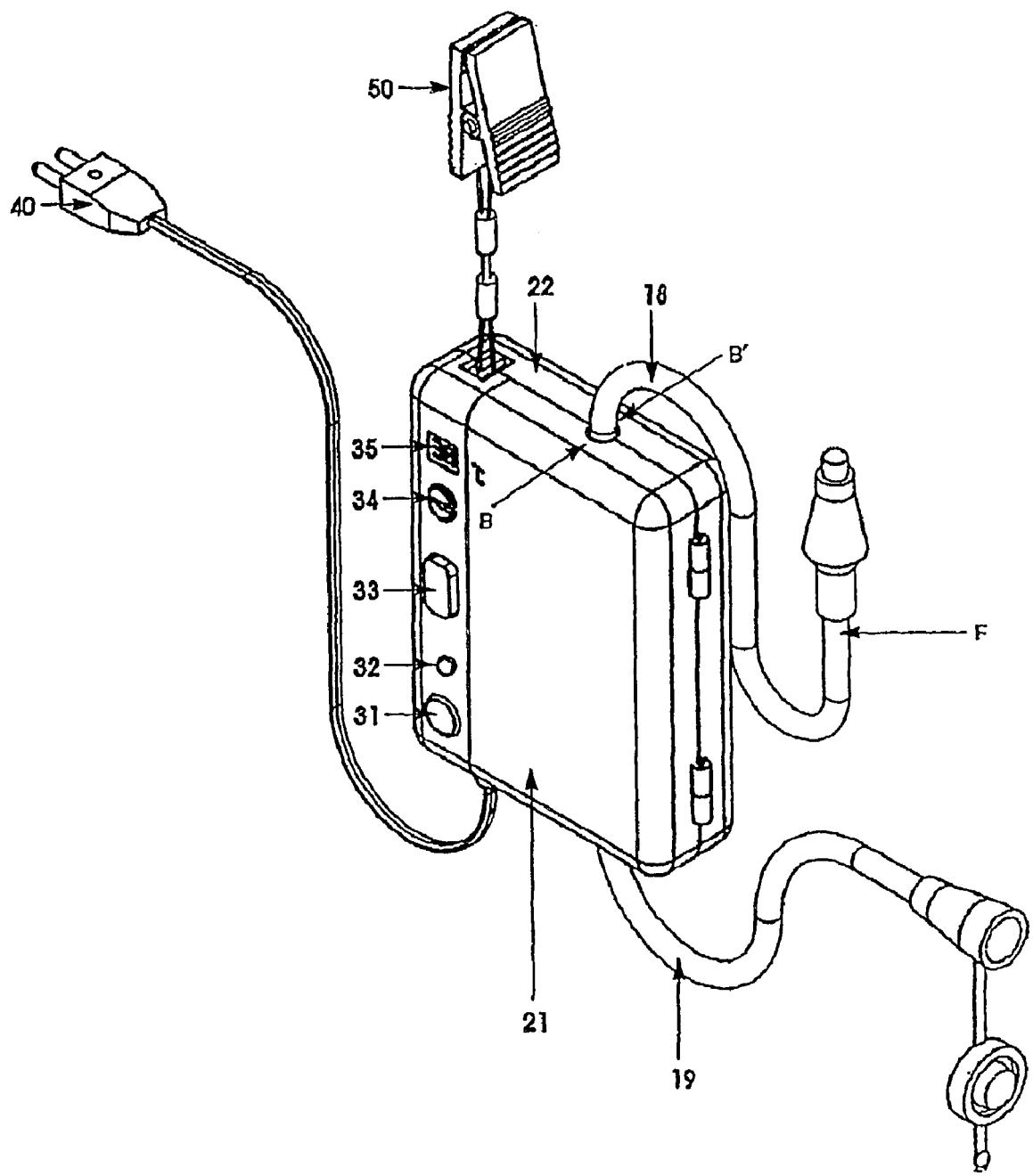

[Fig. 1c]
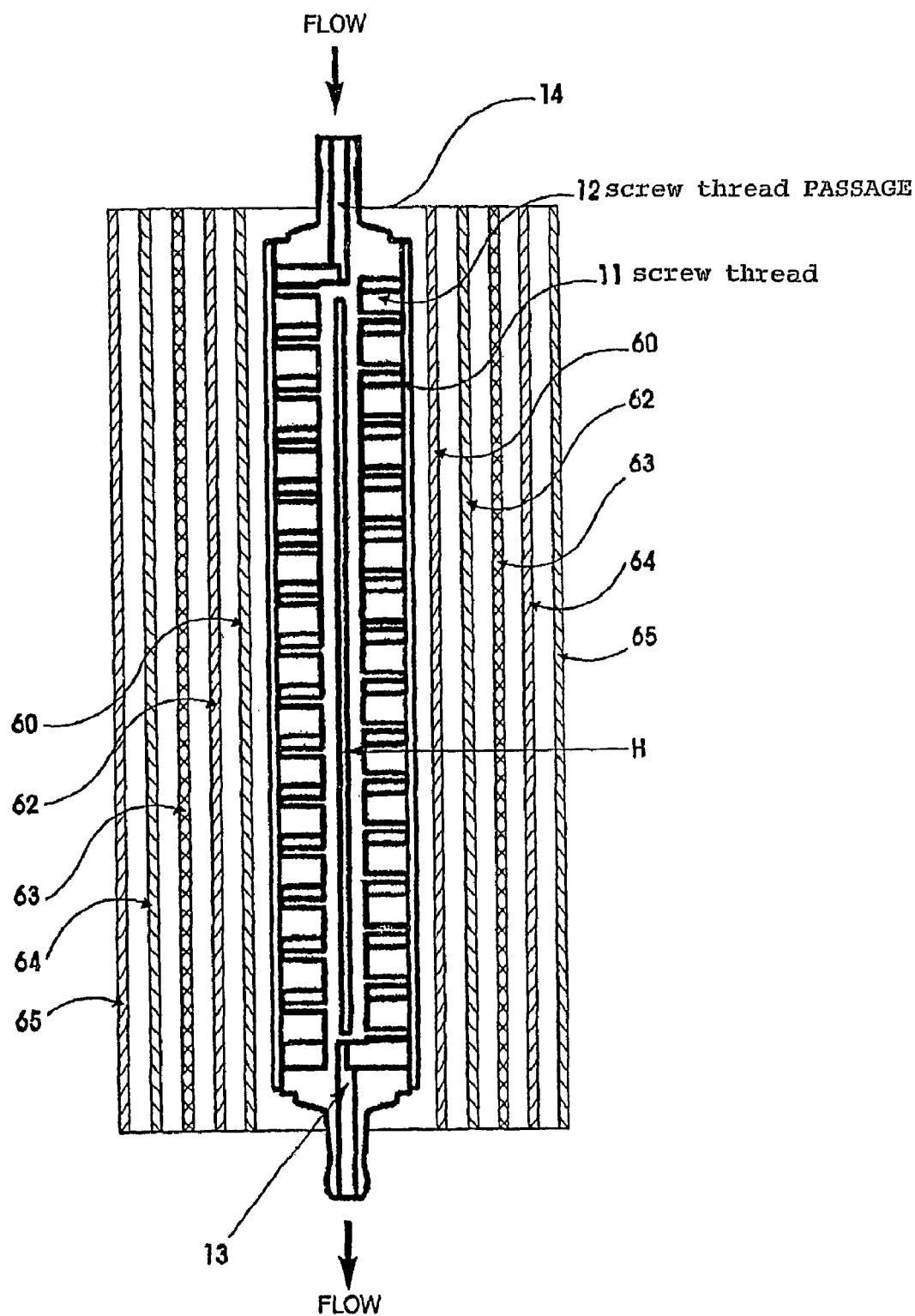

[Fig. 2a]
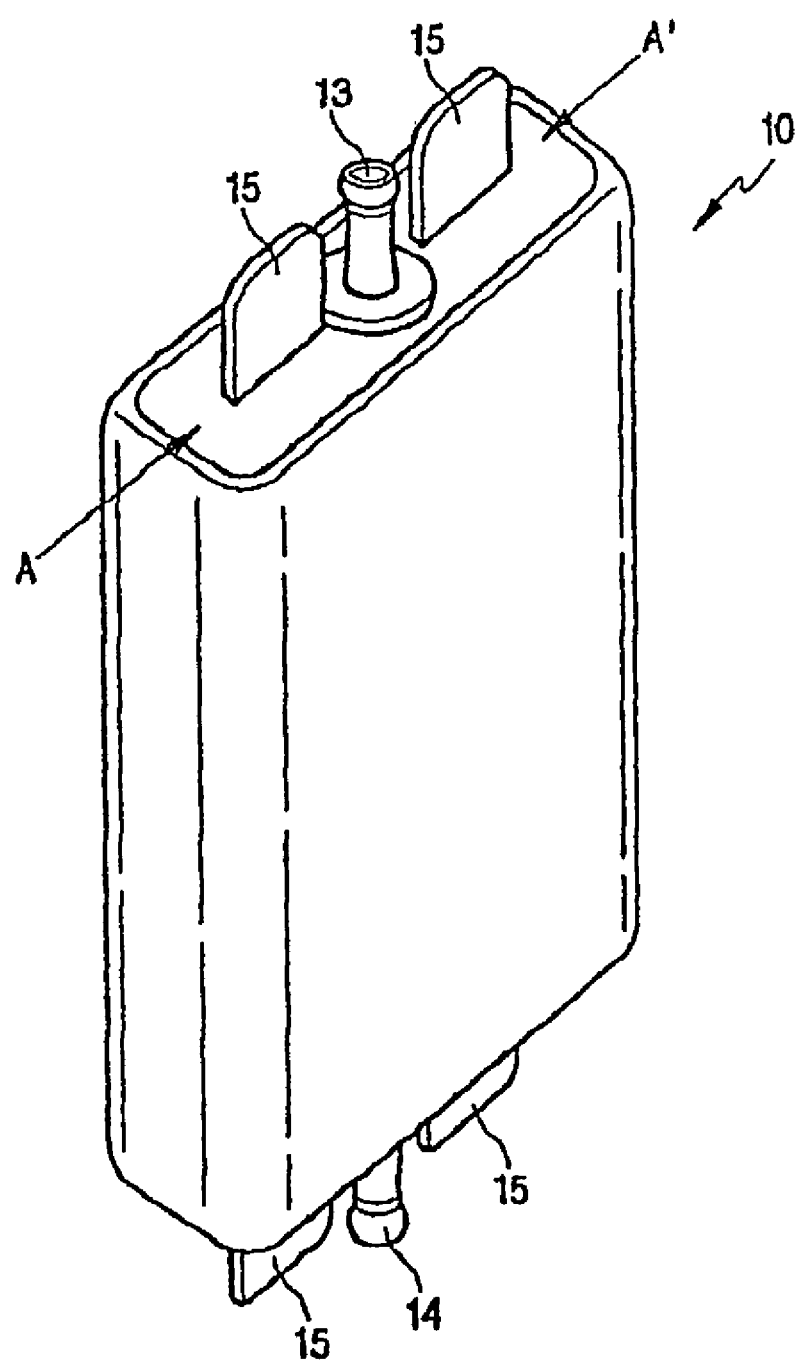

[Fig. 2b]
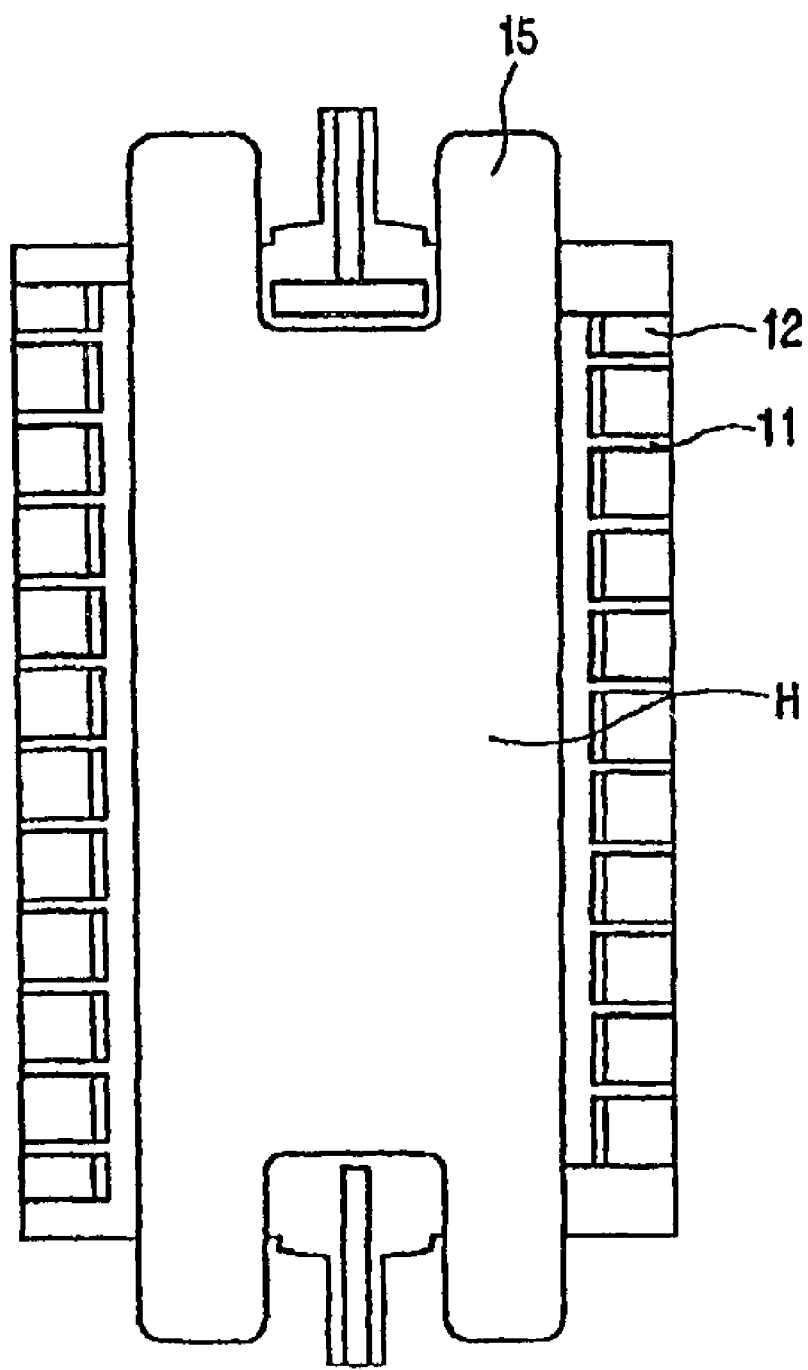

[Fig. 3]
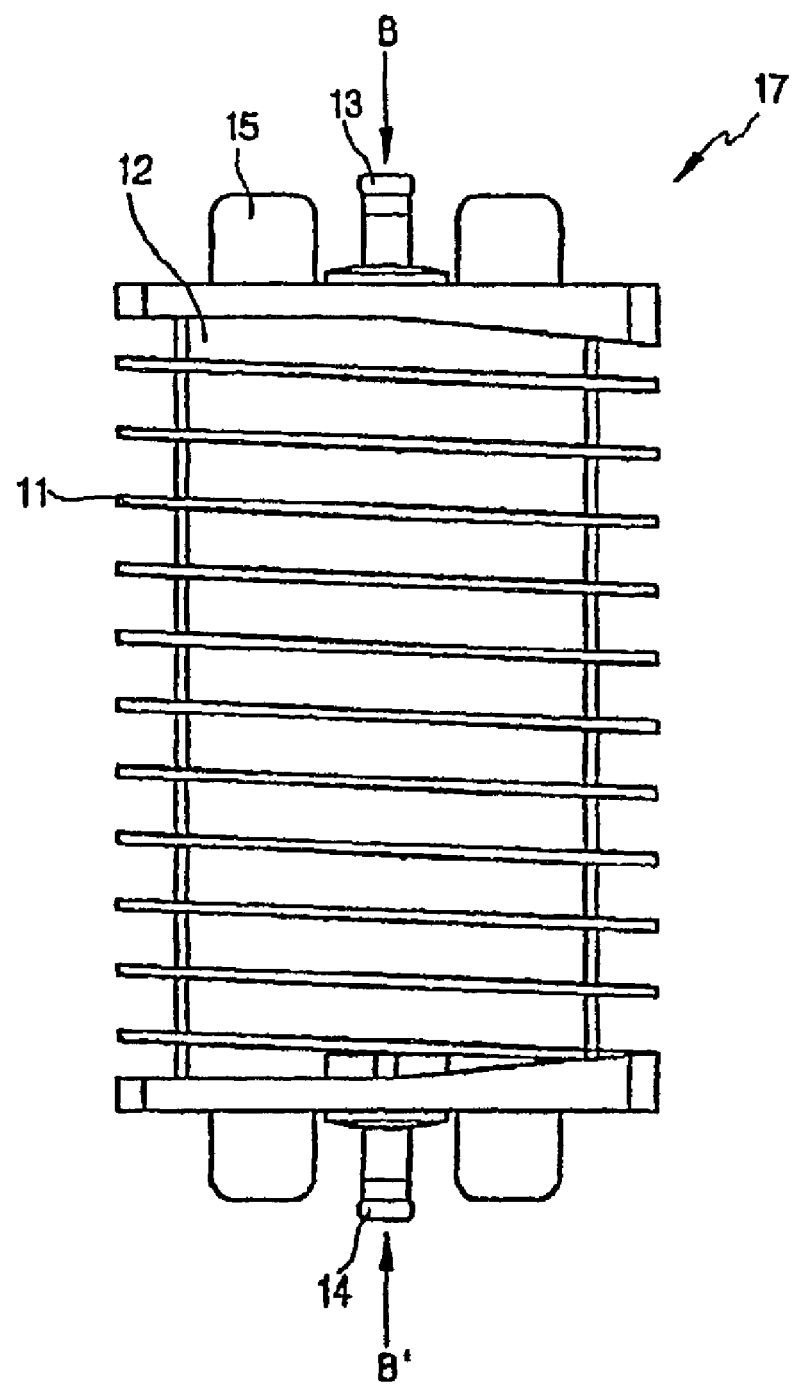

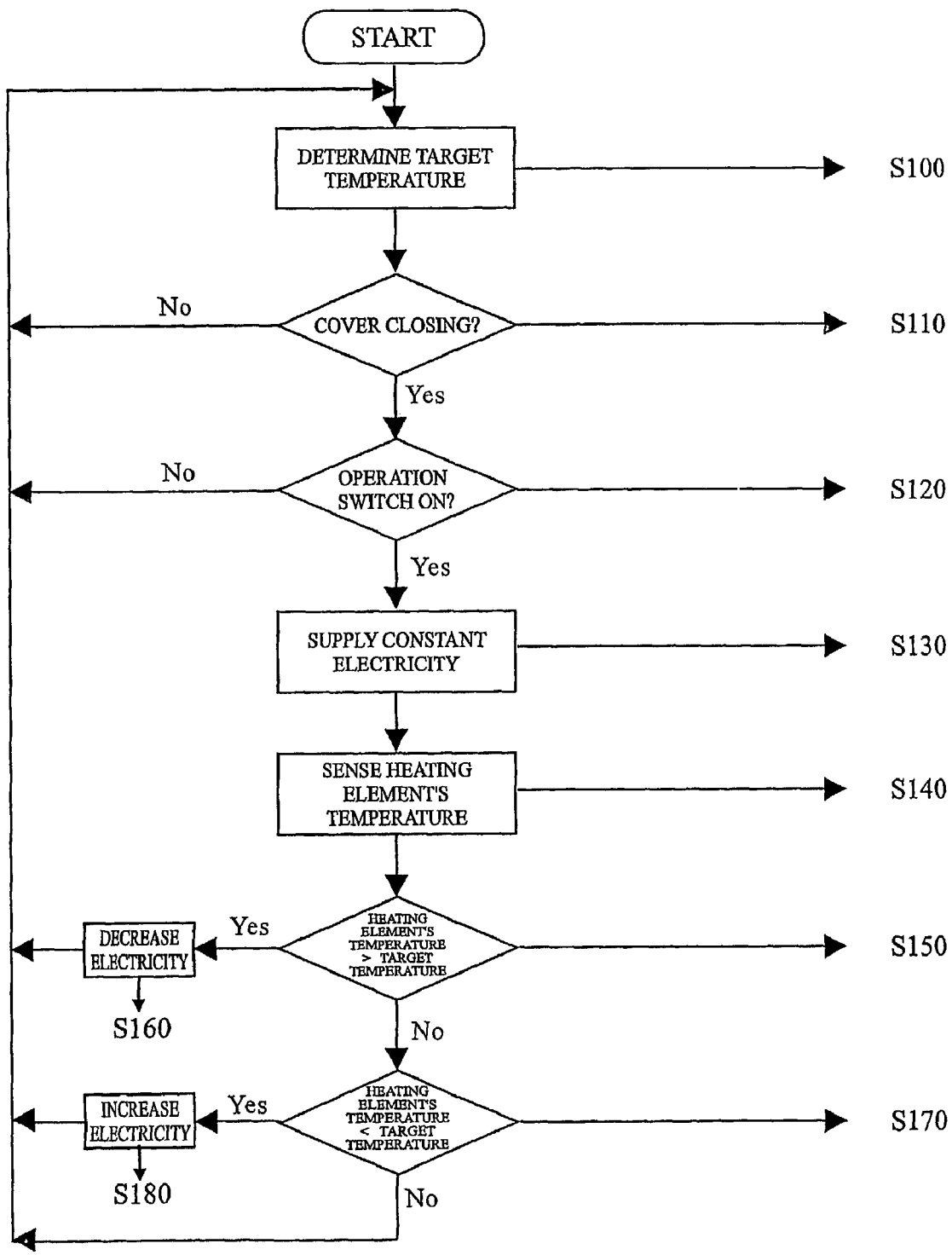
[Fig. 4]

[Fig. 5]
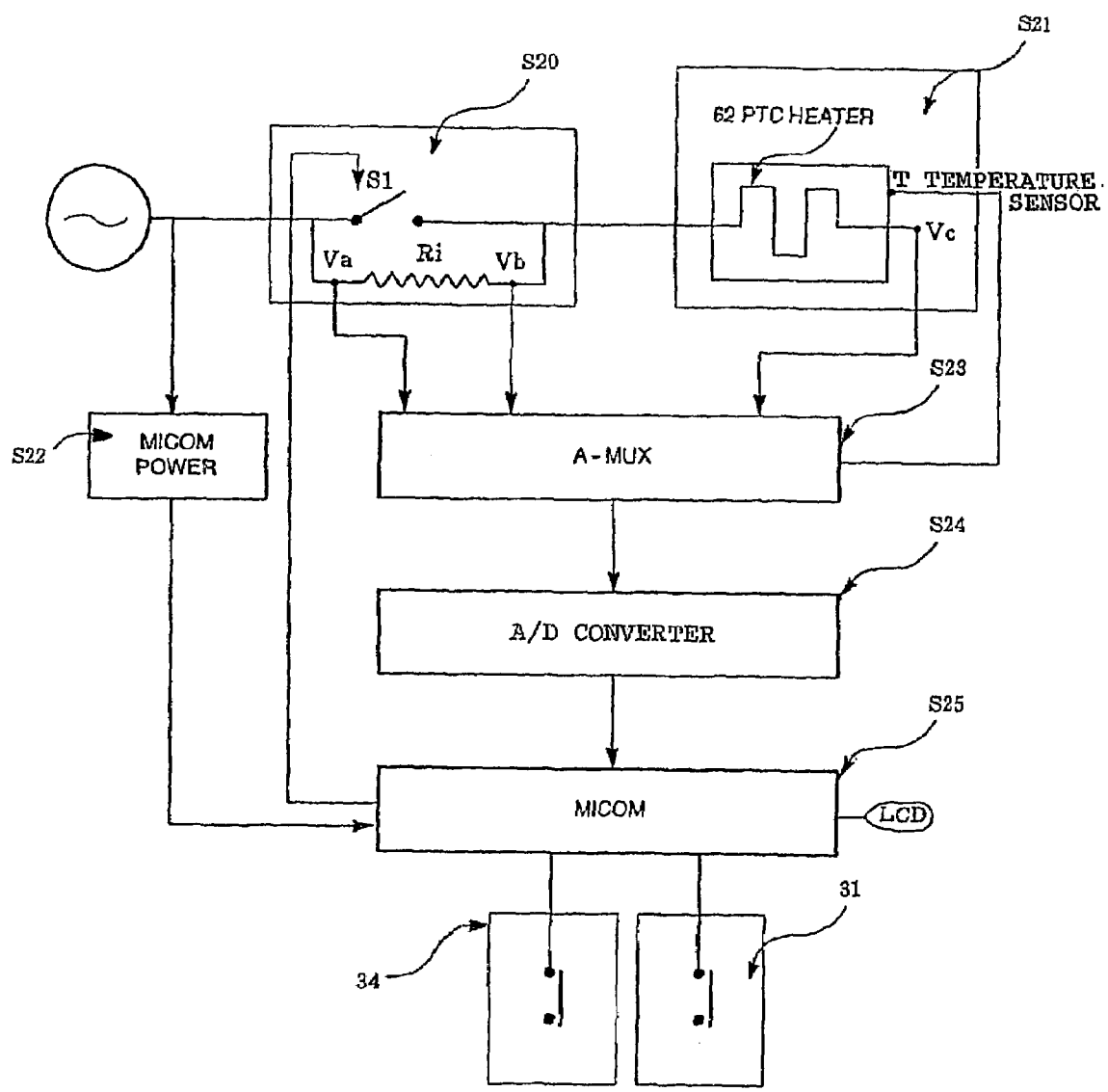

WARMER FOR MEDICAL TREATMENT AND ITS CONTROL METHOD

TECHNICAL FIELD

The present invention relates to a warming device for a medical treatment; and more particularly, to a warming device for a medical treatment, which is capable of preventing a danger of falling of body temperature and alleviating the patient's pain, by making blood temperature similar to body temperature in the event of injection of Ringer's solution fluid or blood transfusion. The warmer according to the invention is lighter, cheaper and simpler in manipulation than a conventional Ringer's solution fluid warming device.

BACKGROUND ART

Conventionally there are a medicine dosage method and an injecting method of injecting chemical material useful for a patient to the human body. The method of injecting the chemicals into the body of a patient, there are a hypodermic injection, an intramuscular injection, and an intravenous injection. Among them, the intravenous injection has been used for injecting injection fluid inside a blood vessel for a long time. For example, in the event of supplying blood in operation or injecting Ringer's solution fluid, the intravenous injection using an instillation injection set is used.

The Ringer's solution fluid is usually kept at lower temperature to prevent a decay or a generation of an alien substance. Blood is generally kept under a refrigerating state in order to prevent a generation of a harmful organism before a blood transfusion. Thus, the temperature of the Ringer's solution fluid or blood usually is kept under 20° C. when the Ringer's solution fluid or blood enters the human body. Therefore, when the Ringer's solution fluid or blood enters the human body, the temperature of the Ringer's solution fluid or transfused blood rises to the temperature of the human body since the body temperature usually is 37° C. In this case, the energy necessary for the temperature increase of the Ringer's solution fluid or blood is supplied by the patient's risen metabolism. Such thermic load causes the body temperature fallen and a coldness sensation point of skin is stimulated. That is, a transfusion of the Ringer's solution fluid or the blood transfusion may cause a sensation of cold pain to the patient or may be a mortal blow to life.

To solve such a problem, Patent No. 130926 of R.O.K disclosed a warmer for a medical treatment and a method therefor, in which the temperature of Ringer's solution fluid or blood was made matched with temperature of the human body before a transfusion into the body 1.

In Patent No. 130926 of R.O.K, in order to control the temperature of the Ringer's solution fluid, a tube is fixed onto an upper part of a panel, and on the upper part of the panel, a first cover is put, and the first cover is fixed to a vertical member through a use of a hinge. Further, a locking device is set in a vertical member confronted with the vertical member having a sticking of the hinge, and the first cover has a sticking of a second cover which contains heat shield material in the inside of an upper part thereof. Inside an overall square-shape container, the tube is inside-installed, and the tube provided inside the square container is warmed by a heating unit of the square container inside.

It is actually difficult to raise temperature of the short tube to a desired temperature and to control the desired temperature by the heating unit of the square container interior, where the warmer for the medical treatment should be warmed in lower temperature below 41.5° C. since a length of the tube in the inside of the square container is short. Even though the high temperature heating device, which may cause ill effects, is used, the device becomes complicated and expensive due to a use of more accurate electronic controlling system.

Furthermore, in a warmer using a conventional Ni—Cr heating element, a tube of Ringer's solution fluid is wound on the surface of the heating element made round, and above that, a cover is closed and locked by a locking device. Thus, whenever using that, there is an inconvenience and a complicated structure that the tube should be wound on the surface of the heating element, and the volume of the warmer must be large since the Ni—Cr heating element is utilized. Also its weight is over 2 kg, so heavy, and its price is high.

DISCLOSURE OF THE INVENTION

Accordingly, the present invention is directed to a warming device for a medical treatment that substantially obviate one or more of the limitations and disadvantages of the related art.

A primary object of the present invention is to provide a warming device for a medical treatment, which is capable of preventing a danger of falling of body temperature by making the blood temperature similar to body temperature in the temperature of Ringer's solution fluid or blood transfusion, and also of alleviating a patient's pain, in the existing Ringer's solution fluid injecting apparatus composed of Ringer's solution fluid, an instillation chamber, a tube and an injection needle, or in a blood transfusion apparatus composed of blood, a blood filtering tube, a tube and an injection needle, wherein the warming device comprises a heat transferring unit which has a cover provided on the body containing a screw thread, the heat transferring unit including the screw thread, a passage where Ringer's solution fluid or blood is passed, a connecting part which is connected to a tube connected to an instillation chamber, and a connecting part which is connected to a tube connected to an injection needle; a cover unit which contains a plate type heating element within upper and lower parts of the cover and which warms the heat transferring unit by stably positioning the heat transferring unit inside the cover; a controlling unit which is constructed by a driving switch, a driving display light, a cover locking button, an up/down button and a temperature representing part on one side of the cover unit, the controlling unit being for controlling temperature inside the cover unit; a power unit for supplying power to the controlling unit; and a fixing unit for fixing the cover unit to a bed.

Another object of the present invention is to provide a warming device for a medical treatment constructed as the above, which is capable of allowing blood or solution fluids to flow most effectively by allowing sufficient time for heat transfer as a pack type, and of ensuring that temperature of a heating element and of an element being warmed is equal by maximizing a contact area, and of making the operation convenient and sanitary in that only a single usage is allowed. The object of the present invention further is to provide a method of utilizing a temperature sensor in adjusting temperature of the heating element, and a method of utilizing a temperature dependence of a PTC heating element's resistance against the temperature in adjusting the temperature, wherein the PTC is the object which is direct-proportioned to temperature in a heating element resistance coefficient. Herewith, the PTC's temperature rises till design temperature, to be thus enabled to be used as more stabilized heating element and enable to provide more advantages in the manufacture.

BRIEF DESCRIPTION OF THE DRAWINGS

The above and other objects and features of the instant invention will become apparent from the following description of preferred embodiments taken in conjunction with the accompanying drawings, in which:

FIG. 1a indicates a perspective view of a warming device for a medical treatment in accordance with the present invention;

FIG. 1b is a perspective view provided when closing a cover shown in FIG. 1a;

FIG. 1c illustrates a front sectional view of B–B' in a warming device for a medical treatment shown in FIG. 1b;

FIG. 2a represents a perspective view of a heat transferring unit shown in FIG. 1a;

FIG. 2b shows a front sectional view of A–A' for a heat transferring unit shown in FIG. 2a;

FIG. 3 depicts a front view of a body 17 which has a screw thread provided in such a state that a cover of a heat transferring unit shown in FIG. 2a is opened;

FIG. 4 is a flowchart showing a procedure of warming Ringer's solution fluid in the present invention; and FIG. 5 sets forth a flowchart of a controlling unit for controlling temperature inside a cover unit.

BEST MODE FOR CARRYING OUT THE INVENTION

Reference will now be made in detail to the preferred embodiments of the present invention, examples of which are illustrated in the accompanying drawing.

FIG. 1a is a perspective view showing an overall structure of a warming device for a medical treatment in accordance with the present invention, and is a state view in which a cover upper part 21 and a cover lower part 22 are opened, and a heat transferring unit 10 is installed in a cover interior space 23 in a lower part of the cover. As shown in FIG. 1c, a heating element 63 and a dielectric element 62 are respectively set inside the cover upper part 21 and the cover lower part 22, and on its upper and lower faces contacted with the heat transferring unit 10, a shape of a heat transferring unit is made of material 60 having a prominent heat transfer efficiency so that the cover upper and lower parts can serve as a role of transferring heat to the heat transferring unit 10, and further, inside the cover of a side which is not contacted with the heat transferring unit 10, heat shield material 64 is entered to prevent a heat loss toward the outside.

FIG. 1b is a perspective view provided when closing a cover of a warming device for a medical treatment shown in FIG. 1a.

FIG. 1c is a front sectional view of B–B' in the warming device for the medical treatment shown in FIG. 1b.

FIG. 2a represents a perspective view of the heat transferring unit 10 which is constructed so that Ringer's solution fluid can pass through in the warming device for the medical treatment shown in FIG. 1, and FIG. 2b shows a front sectional view of A–A' for the heat transferring unit 10 shown in FIG. 2a, and FIG. 3 indicates a front view of a body 17 which has a screw thread provided in such a state that the cover of the heat transferring unit 10 shown in FIG. 2a is opened.

The construction of the inventive warming device for the medical treatment is described as follows, referring to FIGS. 1a through 3.

In the existing Ringer's solution fluid injecting device (not shown in the drawings) composed of a Ringer's bottle, an instillation chamber, a tube and an injection needle, Ringer's solution fluid is passed through a passage 12 between screw threads 11, and in the body 17 having the screw thread, heat transfer material H having a heat transferring terminal 15, or a heating element H having an electrode terminal 15, can be additionally installed crossing the body 17 which has the screw thread. Further, in upper and lower parts of the body 17 having the screw thread, each connecting part 13, 14 connected to a tube is set, and the body 17 having the screw thread has the cover and is stably installed in the internal space 23 of the cover unit as shown in FIG. 1a, under such a state that the cover is closed.

The purpose that the screw thread is contained into the body having that screw thread is to pass the Ringer's solution fluid or blood through a long passage 12 provided between the screw threads and to enlarge an area contacted with the heating element and prolong a contact time so as to easily make temperature of the Ringer's solution fluid or blood, desired temperature, through a warming of low temperature. In other words, the invention can be characterized in an aspect of improving conventional problems that the temperature is maintained by rapidly warming a conventional tube, and that determined temperature and target temperature are compared with each other and electricity power is supplied by measuring temperature of the tube fixed into the interior space or outlet temperature of the tube as the target temperature, to thus transfer heat to the Ringer's solution fluid of the tube interior. Also, the invention can be characterized in an aspect of improving conventional problems such as a heat inertia correction problem and a position problem of a temperature sensor, namely, a difficulty of discriminating and sensing the heating element and an element being warmed in a case of an installation inside the heating element, or a difficulty of sensing exact temperature owing to an influence of outside environment, for example, an influence of wind and the indoor temperature, in a case of an installation outside the heating element, which causes a difficulty in an installation of the temperature sensor. That is, the invention has features that the temperature sensor directly senses and controls temperature of the heating element by meeting the target temperature with that of the heating element, to thereby, constantly, fix the heating element's temperature to desired temperature in comparison with the existing method nearly impossible in manufacture, and to equalize the heating element's temperature to the target temperature according that the Ringer's solution fluid passes through a wide surface area between screw threads of the heat transferring unit 10 which is stably installed inside the heating element and through the long passage 12, then enters the human body.

As described above, it is effectively invented to set the structure having the screw thread so as to efficiently transfer heat and set the heat transfer material having a heat transferring terminal in the inside thereof or the heating element having an electrode terminal. In addition, material of the body having the screw thread may be medical material such as PVC or plastic, and can be made small in size. Therefore, it can be curtailed in material costs and can be simply replaced since the heat transferring unit 10 can be manufactured and utilized for a single usage only.

Herewith, material having a prominent heat transfer rate or a heating element is put inside the body 17 having the screw thread. Thus, when the Ringer's solution fluid is passed through the passage 12 between the screw threads, not only the cover upper and lower parts 21, 22 but also an interior space of the body having the screw thread can receive the heat transfer from the material having the prominent heat transfer rate or from the heating element H. Thereby, a length of the passage between the screw threads, which is necessary for desired temperature as the target temperature, is lessened in comparison with a case that nothing is in the interior space. Accordingly there is an advantage that the volume of the body having the screw thread becomes small.

Meanwhile, a fixing unit 50 is provided to fix the warming device to a bed during that the Ringer's solution fluid enters the human body, and the body 17 having the screw thread of the heat transferring unit 10 is made under a state that the connecting part 13, 14 has an installation of a tube 18 containing a combination aperture so as to be easily combined with the tube which is connected to an injection needle, as shown in FIG. 1*a*. For example, a combination aperture of the tube 19 which has the combination aperture is same as the combination aperture structure of a butterfly needle named as another name, the butterfly needle being provided in the open market.

Furthermore, a filter F for filtering air bubble generated in warming is installed on one side of the tube 18 disposed between the connecting aperture 13 of the heat transferring unit and the injection needle.

FIG. 4 is a flowchart showing a method of warming the Ringer's solution fluid or blood which passes through the Ringer's solution fluid warming device in the above embodiment, which is described in detail, as follows.

The target temperature is determined by an up/down button 34, and the determined temperature is represented on a temperature display part 35. Next, when the cover unit is closed in a step S110 and power is turned ON, constant electricity proper to the determined temperature is supplied in a step S130. Subsequently, a controlling unit senses temperature of the heating element in a step S140, and temperature of the heating element and the target temperature are compared with each other in a step S150. When the temperature of the heating element is higher than the target temperature, the electricity is reduced in a step S160, and oppositely, when the temperature of the heating element is smaller than the target temperature, the electricity is increased so that the temperature of the heating element provided in the inside of the cover unit is constantly maintained as the target temperature. Thereby, when fluid entered through the connecting aperture 14 of the heat transferring unit is discharged from the outlet 13 of the heat transferring unit connected to the injection needle through the passage 12 provided between the screw threads, the temperature of the Ringer's solution fluid or blood becomes same as the target temperature, and then it enters the human body.

When a driving switch 31 is turned on by connecting electricity power 40 of the inventive Ringer's solution fluid warming device, a driving display light 32 is always lighted during a turning-on of the driving switch. Only when the cover upper 21 and the cover lower part 22 are closed, the driving switch 31 can be lighted up, and when the cover is opened, the driving switch 33 is turned off, so as to remove a danger of an electric leakage. Thus, after connecting the electricity power, the cover is closed and the driving switch 31 is lighted up, then the driving display light 32 is lighted up. Further, when a user determines desired temperature by using the up/down button 34, the desired temperature as target temperature is displayed on the temperature display part 35. When the Ringer's solution fluid or blood is passed through the heat transferring unit 10, the Ringer's solution fluid or blood is warmed as well as the temperature represented on the temperature display part 35. The tube connected to the instillation chamber and the tube connected to the injection needle are individually connected to the connecting parts 13, 14, then, the Ringer's solution fluid or blood flows into the tube through the instillation chamber, and this fluid is passed through the passage 12 which is long and wide in a warming surface area, the passage being between the screw threads provided in the body 17 which has that screw thread of the heat transferring unit. During that, the fluid is warmed in low temperature and becomes the target temperature, and flows through the tube having a sticking of the injection needle, and is finally injected into the human body.

FIG. 5 is a flowchart for a method of controlling temperature of a heating element provided in the cover unit when warming Ringer's solution fluid or blood which passes through the warming device for a medical treatment, in an embodiment of the present invention. Also FIG. 5 is the flowchart representing a method of controlling temperature of the heating element which contains a 62 PTC heating element installed in a step S21, through the temperature sensor, and a method of controlling temperature through a resistance measurement of the PTC heating element by using a characteristic of the PTC heating element.

First, a temperature controlling system through the temperature sensor is a general method. That is, a value read in an S23 A-MUX through a temperature sensor T installed in the step S21 is converted in an S24 A/D converter so that an S25 MICOM can read it well, and then, the S25 MICOM controls a switch S1 of S20, and when it is lower than target temperature, the S25 MICOM increases the electricity amount flowing in the heating element. In case that there is a possibility of rising more than the target temperature, the S25 MICOM lessens the electricity amount flowing in the heating element so that the heating element heats appropriately to determination temperature.

Another method in the temperature controlling system using the PTC heating element's characteristic is described as follows.

In this temperature controlling system using the PTC heating element's characteristic, a temperature dependence of a 62 PTC heating element resistance can be already known in manufacture, the 62 PTC heating element being the heating element in which a resistance coefficient is direct-proportioned to temperature, and momental current iPTC flowing in the 62PTC can be known by using a control switch S1 of S20 and a resistance Ri knowing a resistance value under such a state that temperature dependence data or a formula of the PTC resistance is inputted into the S25 MICOM. When knowing the iPTC, a resistance value of the 62PTC heating element of S21 can be known, and when knowing this resistance value, temperature of the 62PTC heating element can be known by the already inputted PTC data or temperature dependence formula.

When knowing the temperature of the 62PTC heating element, the electricity amount is controlled by the S1 control switch so as to heat as well as the target temperature.

Describing such method more in detail, as shown in S20, the S1 control switch controlled by the S25 MICOM and an optional resistance Ri already knowing the resistance value are set. Since a resistance Ri value of S20 is already known, under a momental OFF state of the S1 switch in the midst of an operation, the MICOM of S25 recognizes voltage Va, Vb of S20, and voltage Vc of S21 through an S23 A-MUX and an S24 A/D converter. Through this recognized voltage Va, Vb values, it can be known that the iPTC as the momental current flowing in the 62PTC heating element is provided as 'iPTC=Vb−Va/Ri' by an Ohm's law. When knowing this iPTC, it can be known 'RPTC=Vc−Vb/iPTC' as 62PTC resistance value changed according to temperature. Accordingly, the S25 MICOM can know temperature of the PTC heating element by the above measured PTC heating element's resistance value through the temperature dependence data or formula of the already inputted PTC heating element. When knowing the temperature, the S25 MICOM compares this temperature with the determination temperature. When the temperature of the 62PTC heating element is lower than the determination temperature, the electricity amount is increased through the S1 control switch of S20. In case that there is a possibility that the temperature of the 62PTC heating element becomes higher than the determination temperature, the electricity amount decreases. Such overall procedures are repeated continuously, controlling so as to be matched with the determination temperature.

Further, a reference number 34 represents the up/down switch and 31 a driving switch, and S22 a driving power device for driving the MICOM.

INDUSTRIAL APPLICABILITY

As aforementioned, in accordance with the present invention, a warming device for a medical treatment can prevent a danger of falling of body temperature by making the temperature of blood temperature similar to body temperature in the injection of Ringer's solution fluid or blood transfusion, and also, can aleviate patient's pain and can speed up the injection of Ringer's solution fluid or blood.

In addition, the volume can become smaller than a conventional warming device and a weight is lighter, and there is an effect that its manipulation is simple by using a cheap heat transferring unit. In addition, a product is light by using a plate type heating element containing a PTC, and a danger of overheating can be reduced by a characteristic of the heating element which rises only to constant temperature when utilizing the PTC heating element. Also, a temperature control is possible even without a temperature sensor by controlling temperature through a characteristic use of the PTC heating element, that is, manufacturing expenses can be curtailed and a manufacture thereof is simple. Furthermore, for more exact temperature control, a temperature control using the PTC heating element's characteristic and a control using a temperature sensor can be performed simultaneously.

Although the invention has been shown and described with respect to the preferred embodiments, it will be understood by those skilled in the art that various changes and modifications may be made without departing from the spirit and scope of the invention as defined in the following claims.

What is claimed is:

1. A warming device for a medical treatment comprising:
   a heat transferring unit which is composed of a body having a screw thread, a passage between the screw threads where Ringer's solution fluid or blood is passed, a connecting part disposed on one side ending part of the body and connected to an instillation chamber, and a connecting part disposed on another side ending part of the body and connected to an injection needle;
   a covering unit which contains a heating element and a dielectric element within cover upper and lower parts and which warms the heat transferring unit by stably positioning the heat transferring unit inside the covering unit;
   a controlling unit which is constructed by a driving switch, a driving display light, a cover locking button, an up/down button and a temperature representing part on one side of the covering unit, said controlling unit being for controlling temperature inside the covering unit; and
   a power unit for supplying power electricity to the controlling unit.

2. The device of claim 1, wherein said covering unit is provided with a fixing unit for fixing the covering unit to a bed etc, said fixing unit being installed on one side of the covering unit.

3. The device of claim 1, wherein said heat transferring unit is gained by inserting heat transfer material having a heat transferring terminal into the inside of the body which has the screw thread.

4. The device of claim 1, wherein said heat transferring unit is gotten by inserting a heating element having an electrode terminal into the inside of the body which has the screw thread.

5. The device of claim 1, wherein on one side of a tube which is disposed between a connecting aperture of the heat transferring unit and an injection needle, a filter for filtering air bubble generated in warming is installed.

6. The device of claim 1, wherein said power unit does not supply the power electricity to the heating element when the covering unit is opened.

7. The device of claim 1, wherein said power unit supplies the power electricity to the heating element only when the driving switch is turned ON, even though the covering unit is closed.

8. The device of claim 1, wherein said covering unit is heat-shielded by heat shield material.

9. The device of claim 1, wherein said heating element contains a PTC heating element.

10. The device of claim 1, wherein said controlling unit includes a function of controlling the temperature by using a resistance characteristic based on temperature of the PTC heating element.

11. The device of claim 1, wherein said controlling unit includes a function of controlling the temperature by utilizing a temperature sensor.

* * * * *